Figure 1:
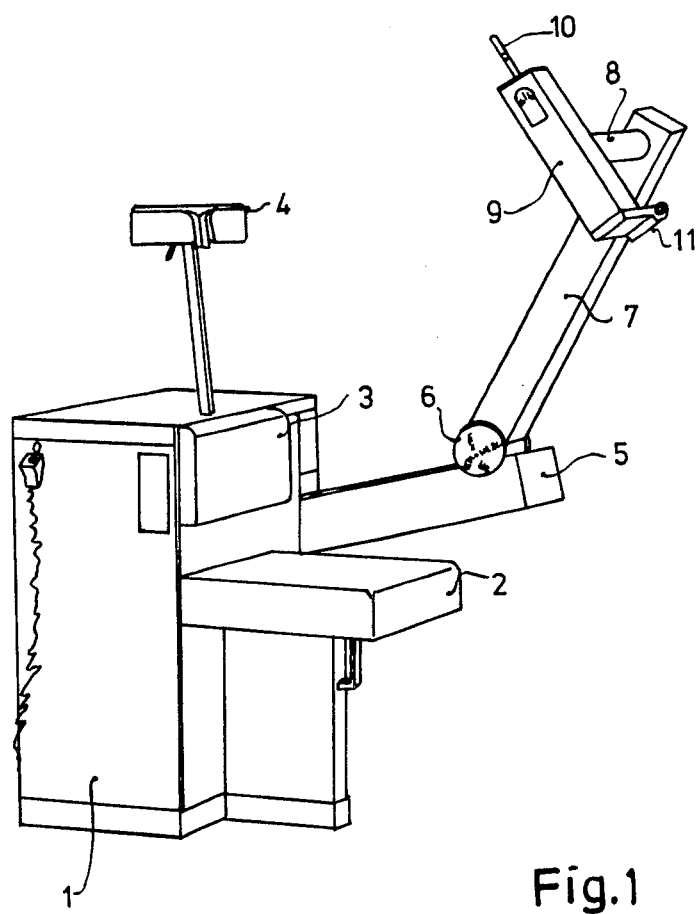

United States Patent [19]

Schmedemann

[11] 4,101,779

[45] Jul. 18, 1978

[54] APPARATUS FOR MECHANICALLY SUPPORTING A MEDICAL DEVICE IN A PLANE

[75] Inventor: Walter Schmedemann, Hamburg, Fed. Rep. of Germany

[73] Assignee: U.S. Philips Corporation, New York, N.Y.

[21] Appl. No.: 712,923

[22] Filed: Aug. 9, 1976

[30] Foreign Application Priority Data

Aug. 13, 1975 [DE]  Fed. Rep. of Germany ....... 2536081

[51] Int. Cl.² ............................................ H01J 35/16
[52] U.S. Cl. ................................ 250/445 R; 250/523; 32/22
[58] Field of Search ............... 250/445 R, 445 T, 446, 250/523; 32/22

[56] References Cited

U.S. PATENT DOCUMENTS

| | | | |
|---|---|---|---|
| 2,156,170 | 4/1939 | Augustin et al. | 250/445 T |
| 2,167,115 | 7/1939 | Kieffer | 250/445 T |
| 3,770,955 | 11/1973 | Tomita et al. | 250/445 T |
| 4,000,424 | 12/1976 | Rouge et al. | 250/445 T |

*Primary Examiner*—Bruce C. Anderson
*Attorney, Agent, or Firm*—Frank R. Trifari

[57] ABSTRACT

Apparatus comprising a parallelogram which is movable in one plane and which is formed by a first and a second coupling rod and a part of a first and a second supporting rod for a medical device and a counterweight therefor, respectively. The coupling rods are pivotably connected near one end to the first supporting rod and are pivotably connected to the second supporting rod near their other end. The parallelogram is pivotable about a stationary shaft which extends perpendicularly to the plane of movement. This shaft is situated between the two pivots of a coupling rod.

3 Claims, 3 Drawing Figures

APPARATUS FOR MECHANICALLY SUPPORTING A MEDICAL DEVICE IN A PLANE

The invention relates to an X-ray apparatus comprising an X-ray source which is displaceable in one plane and which is connected to a first supporting rod, and also comprising a counterweight which is connected to a second supporting rod, the two supporting rods being interconnected by way of a first and a second coupling rod which form a parallelogram in conjunction with the supporting rods, the said parallelogram being pivotable about a stationary shaft which extends perpendicularly to the plane of movement of the X-ray source.

In a known X-ray apparatus of the kind set forth (German Patent Specification No. 939,348), the stationary pivot shaft is situated in a corner point of the pivotable parallelogram. The supporting rods of X-ray source and counterweight are pivotably coupled to each other at the corner point of the parallelogram diametrically opposite the said corner point.

The known X-ray apparatus has a drawback in that the dimensions of the parallelogram must be comparatively large to prevent the counterweight from having to be inadmissibly heavy or the range of movement of the X-ray source from being substantially limited. Comparatively large dimensions of the sides of the parallelogram, however, increase the risk of a patient being clamped in the parallelogram. Enclosure of the parallelogram in order to obtain a closed construction leads to an undesired increase in the weight of an apparatus in the case of comparatively large parallelograms.

The invention has for its object to provide an X-ray apparatus in which the weight ratio of X-ray source and counterweight is in principle independent of the length of the supporting rods which forms part of the parallelogram, so that a comparatively small parallelogram is feasible.

To this end, an X-ray apparatus in accordance with the invention is characterized in that the two coupling rods are pivotably connected near one end to the first supporting rod and are pivotably connected to the second supporting rod near their other end, the stationary pivot shaft of the parallelogram being situated between the two ends of one of the coupling rods.

Because the stationary pivot shaft of the parallelogram is situated between the ends of a coupling rod and because each coupling rod constitutes a direct link between the two supporting rods, the length of the supporting rods which forms part of the parallelogram is of no importance in the balance equation obtained when the balance of moments of the forces of weight of X-ray source and counterweight is taken around the stationary pivot shaft.

This means that the parallelogram can be reduced in comparison with the known X-ray apparatus, so that the rish of clamping is eliminated. Moreover, the parallelogram can be designed as a closed construction without giving rise to and undesired weight increase.

A special embodiment of an X-ray apparatus in accordance with the invention is characterized in that the coupling rod which is pivotable about the stationary shaft has a hollow profile wherethrough the other coupling rod extends.

The invention will be described in detail hereinafter with reference to the drawing.

FIG. 1 is a perspective view of a preferred embodiment of an X-ray apparatus in accordance with the invention.

Figure 2:
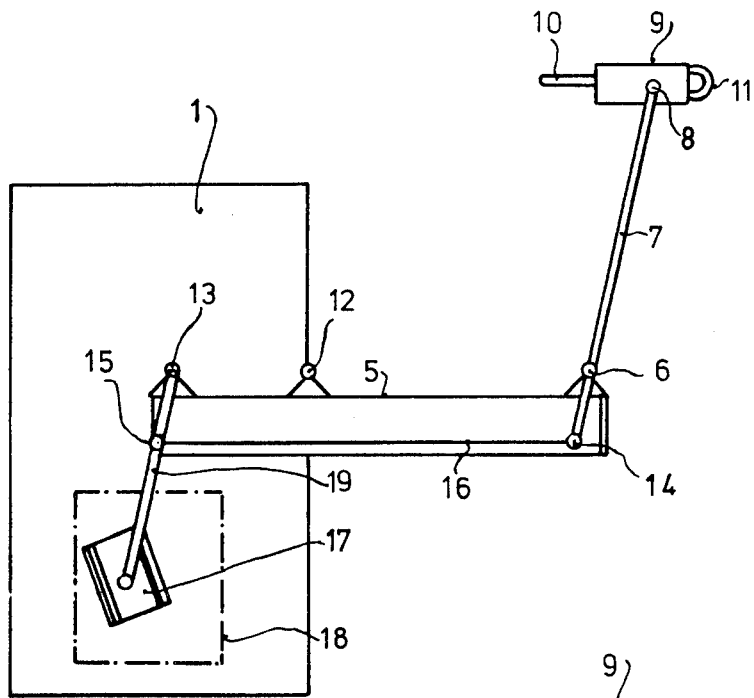

FIG. 2 diagrammatically shows the X-ray apparatus of FIG. 1.

Figure 3:
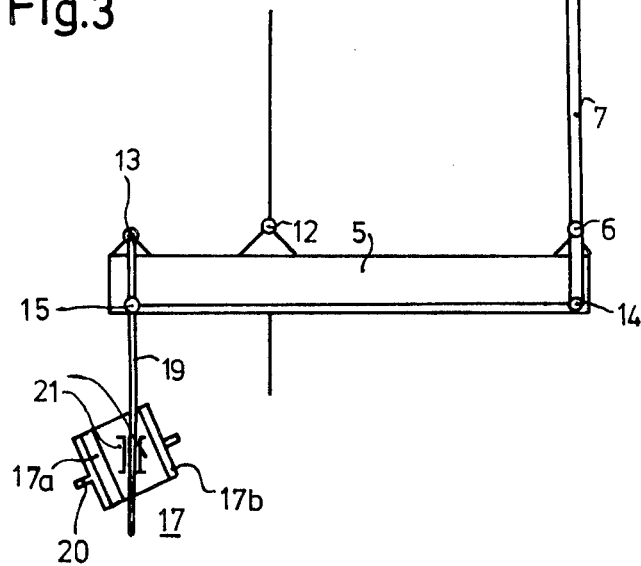

FIG. 3 shows the X-ray apparatus of FIGS. 1 and 2, the counterweight being shown in more detail.

The embodiment shown in FIG. 1 concerns an X-ray apparatus for dental examination. The invention is applicable, however, to any apparatus in which a parallelogram is used in conjunction with a manually displaceable, counter-balanced X-ray source and/or other fluoroscopy or examination and/or treatment device, for example, for the displacement mechanism of a dental drill. The apparatus comprises a housing 1 which is provided on the front with a seat 2 and a back rest 3 for a patient. Behind the back rest 3 there is provided a head rest 4 whose height can be adjusted. The X-ray source 9 comprises an X-ray source having a hollow anode 10, and also comprises a grip 11 by means of which the X-ray source can be moved and by which an electromagnetic brake (not shown) for arresting the X-ray source in an arbitrary position can be operated. The X-ray source 9 is rotatable about a shaft 8 mounted on a first supporting rod 7. The first supporting rod 7 is pivotable about a shaft 6 provided on a first coupling rod 5. The coupling rod 5 is pivotable about a stationary pivot shaft 12 secured in the housing 1. Near its end which is remote from the pivot shaft 6, the coupling rod 5 is pivotably connected (at 13) to a second supporting rod 19 which is provided with a counterweight 17.

The rods 5 and 7 are situated in a vertical plane of movement which extends perpendicularly to a symmetry plane defined by the patient chair 2, the back rest 3 and the head rest 4. The shafts 6, 8, 12 and 13 are perpendicular to this plane of movement.

The first coupling rod 5 and the first supporting rod 7 have a hollow profile so that through these rods a cable can be passed from the housing powering the X-ray source 9. One end of a second coupling rod 16 is pivotably secured (at 14) to the end of the supporting rod 7 which is remote from the X-ray source 9. The other end of the second coupling rod 16 is pivotably connected (at 15) to the rod 19 which supports the counterweight 17. The pivots 14 and 15 are situated so that the coupling rod 16 extends parallel to the first coupling rod. The supporting rods 7 and 19 are parallel to each other. The distance between the pivots 14 and 15 equals the distance between the pivots 6 and 13, so that a parallelogram is formed by the coupling rods 5 and 16 and the supporting rods 7 and 19.

During movement of the X-ray source 9, the counterweight 17 describes a traject, due to the action of the parallelogram, which corresponds to the traject of the X-ray source. The ratio between the distances completed by the X-ray source on the one side and by the counterweight on the other side is dependent of the position of the pivot shaft 12 on the first coupling rod 5 and also on the length of the first supporting rod 7 (between the shafts 6 and 8) relative to the length of the second supporting rod 19 between the shaft 13 and the point at which the counterweight 17 acts.

For limiting the movement of the X-ray source, use can be made of a template 18 (denoted by stroke-dot lines in FIG. 2) which is mounted in the housing 1 and which is engaged by a follower pin (not shown) which is mounted on the supporting rod 19. Furthermore, electromagnetic braking of the X-ray source in an arbitrary position within the range of movement defined by the template 18 can be realized by mounting electromagnets on the rod 19, the said electromagnets cooperating with a portion of the housing which is magnetically conductive at least in this range. The template 18 can be secured in the housing by means of a damping material in order to reduce the risk of vibration.

Accurate weight compensation can be effected as follows.

First, the first supporting rod 7 is placed in a vertical position and the first coupling rod 5 is placed in a horizontal position (FIG. 3). The counterweight 17 is chosen so that the first coupling rod 5 is in a state of equilibrium. If the X-ray source subsequently tends to move the left or the right anyway, tare plates 17a and 17b, detachably included in the counterweight 17, can be moved so that a state of equilibrium is reached.

Subsequently, the first supporting rod 7 and the first coupling rod 5 are placed in an inclined position. The counterweight 17, being displaceable on the rod 19 by way of a slidable clamping device 21 (not elaborated for the sake of simplicity), is shifted so that a state of equilibrium is obtained also in this inclined position.

What is claimed is:

1. Apparatus for mechanically supporting a medical device at any position in a plane, comprising:
   a first supporting rod for pivotably supporting a medical device at a first pivot point along said rod;
   a first coupling rod pivotably connected to said first supporting rod at a second pivot point along said first supporting rod;
   a second coupling rod parallel to said first coupling rod and pivotably connected to said first supporting rod at a third pivot point between said first and second pivot points;
   a counterweight
   a second supporting rod supporting said counterweight at a fourth point along said second supporting rod, said second supporting rod being parallel to said first supporting rod and pivotably connected to said first and second coupling rods at fifth and sixth pivot points respectively, said fifth pivot point being between said fourth and sixth points, said second, third, fifth and sixth pivot points defining a parallelogram; and
   a pivot shaft perpendicular to the plane of the parallelogram and supporting one of said coupling rods at a balance point between the pivot connections thereof with said first and second supporting rods.

2. Apparatus as defined in claim 1 wherein said coupling rod supported by said pivot shaft is hollow and the other of said coupling rods extend therethrough.

3. Apparatus as defined in claim 1 wherein said counterweight is slidably mounted on said second supporting rod.

* * * * *